(12) United States Patent
Maznev

(10) Patent No.: US 7,499,183 B2
(45) Date of Patent: Mar. 3, 2009

(54) METHOD OF MEASURING SUB-MICRON TRENCH STRUCTURES

(75) Inventor: Alexei Maznev, Natick, MA (US)

(73) Assignee: Advanced Metrology Systems, LLC, Natick, MA (US)

( * ) Notice: Subject to any disclaimer, the term of this patent is extended or adjusted under 35 U.S.C. 154(b) by 489 days.

(21) Appl. No.: 10/561,467

(22) PCT Filed: Jun. 23, 2004

(86) PCT No.: PCT/IB2004/050985

§ 371 (c)(1),
(2), (4) Date: Dec. 20, 2005

(87) PCT Pub. No.: WO2004/113883

PCT Pub. Date: Dec. 29, 2004

(65) Prior Publication Data

US 2008/0123080 A1    May 29, 2008

Related U.S. Application Data

(60) Provisional application No. 60/558,071, filed on Mar. 31, 2004, provisional application No. 60/482,099, filed on Jun. 24, 2003.

(51) Int. Cl.
G01B 11/24    (2006.01)
G01B 11/30    (2006.01)

(52) U.S. Cl. .................... 356/601; 356/600; 356/604

(58) Field of Classification Search ............... 356/432, 356/600–613, 625–640; 374/45; 73/800
See application file for complete search history.

(56) References Cited

U.S. PATENT DOCUMENTS

| | | | | |
|---|---|---|---|---|
| 3,978,713 A | * | 9/1976 | Penney | 73/627 |
| 4,710,030 A | * | 12/1987 | Tauc et al. | 356/432 |
| 5,546,811 A | * | 8/1996 | Rogers et al. | 73/800 |
| 5,585,921 A | * | 12/1996 | Pepper et al. | 356/487 |
| 5,633,711 A | * | 5/1997 | Nelson et al. | 356/318 |
| 5,812,261 A | * | 9/1998 | Nelson et al. | 356/318 |
| 5,982,482 A | | 11/1999 | Nelson | |

(Continued)

OTHER PUBLICATIONS

"Microelectronic Film Thickness Determination using a Laser-based Ultrasonic Technique", Logan et al., pp. 347-352. mat. Res. Soc. Symp. Proc. vol. 440.

(Continued)

*Primary Examiner*—L. G Lauchman
*Assistant Examiner*—Jarreas C Underwood
(74) *Attorney, Agent, or Firm*—Goodwin Procter LLP

(57) ABSTRACT

The present invention uses ISTS to measure trenches with near- or sub-micron width. The trenches can be etched in a thin film on in a silicon substrate. One step of the method is exciting the structure by irradiating it with a spatially periodic laser intensity pattern in order to generate surface acoustic waves. Other steps are diffracting a probe laser beam off the thermal grating to form a signal beam; detecting the signal beam as a function of time to generate a signal waveform; determining surface acoustic wave phase velocity from the waveform; and determining at least one property of the trench structures based on the dependence of surface acoustic wave phase velocity on the parameters of the structure.

17 Claims, 9 Drawing Sheets

U.S. PATENT DOCUMENTS

| | | | |
|---|---|---|---|
| 6,081,330 A | 6/2000 | Nelson | |
| 6,174,739 B1 * | 1/2001 | Steffan | 438/7 |
| 6,175,421 B1 | 1/2001 | Fuchs | |
| 6,188,478 B1 | 2/2001 | Fuchs | |
| 6,256,100 B1 * | 7/2001 | Banet et al. | 356/432 |
| 6,587,794 B1 * | 7/2003 | Maznev | 702/28 |
| 6,795,198 B1 * | 9/2004 | Fuchs et al. | 356/521 |
| 6,809,991 B1 * | 10/2004 | Pepper et al. | 367/149 |

OTHER PUBLICATIONS

"Non-Contact Metal Film Metrology using Impulsive Stimulated Thermal Scattering", Gostein et al., pp. 478-488.

"Precise Determination of Thin Metal Film Thickness with Laser-Induced Acoustic Grating Technique", Maznev et al, pp. 195-200. Mat. Res. Soc. Symp. Proc. vol. 591.

"All Optical, Non-Contact Measurement of Copper and Tantalum Films Deposited by PVD and ECD in Blanket Films and Sinle Damascene Strucutures", Banet et al., pp. 419-423.

* cited by examiner

| MEASUREMENT LOCATION | SAW VELOCITY (m/s) |
|---|---|
| UNPATTERNED AREA | 3930 |
| TRENCH ARRAY, PARALLEL | 4016 |
| TRENCH ARRAY, PERPENDICULAR | 2299 |

FIG. 7

METHOD OF MEASURING SUB-MICRON TRENCH STRUCTURES

CROSS REFERENCE TO RELATED APPLICATION

This application claims the benefit of U.S. provisional application Ser. No. 60/482,099 filed Jun. 24, 2003 and U.S. provisional application Ser. No. 60/558,071 filed Mar. 31, 2004 both of which are incorporated herein in whole by reference.

The invention relates to the field of optoacoustic metrology to determine properties of a sample, e.g., a trench structure fabricated on a silicon wafer.

Fabrication of microelectronic devices typically includes multiple patterning steps wherein trench structures (i.e., holes or linear trenches) are fabricated, typically by etching, in a semiconductor substrate or thin film layers deposited on the substrate.

Non-contact optical methods of measuring such structures are in great demand for industrial process monitoring and control. Parameters of most interest for process control applications can include depth, width, and other parameters of the trench structures. In the state-of-the art integrated circuit manufacturing, typical width of the trench structures is of the order of 0.1 μm, while the depth of the trenches may range from under 1 μm to a few microns or more. Non-destructive measurement of such narrow high aspect ratio structures is a challenging problem.

In one known method, described in the prior art U.S. Pat. Nos. 5,812,261, 6,081,330, 6,188,478, herein incorporated by reference, a thin film structure is probed using an impulsive stimulated thermal scattering (ISTS) surface acoustic wave spectrometer. As shown in FIG. 1, in this technique, the sample structure 1 is excited with a short pulse of laser light imaged to form a grating pattern 10 on the sample surface by the interference of two beams 3,3'. Absorption of light under each of the bright stripes of the grating pattern 10 causes local heating of the sample, which results in sudden periodic expansion launching acoustic waves at the sample surface. The acoustic wave propagation can be seen in enlarged portion 8. As this surface acoustic wave (SAW) propagates in the plane of the film, it also modulates the diffracted signal beam 6' intensity, resulting in an oscillatory component (henceforth "acoustic component") in the detected signal.

The above-described technique has been employed to measure the thickness of film layers by analysis of the SAW frequency spectrum.

If a film is patterned, i.e., by etching, ISTS is useful for measuring the etch depth if the size of the etched area is large compared to the SAW wavelength (i.e., typically 2-10 μm). This prior art method will not work for measurement of a surface profile of a bulk sample, such as a silicon wafer. In addition, it is the smaller features (i.e., on the order of 0.1 μm) that are most likely to be misprocessed during lithography and etching. Consequently, these relatively small features require process control metrology.

In one extension of the ISTS technique described in U.S. Pat. No. 6,256,100, the method described above is applied to measure the effective thickness of composite structures formed of narrow (i.e. micron or submicron width) trenches etched in dielectric material and filled with metal. However, this method had not been applied to measuring trench structures prior to metal filling.

In addition, no studies have been done for high-aspect-ratio sub-micron structures which are of the most interest for practical applications.

Accordingly, it would be desirable to provide a method that can measure trench structures on the order of 0.1 μm in width.

The present invention meets the need for a method that can measure trench structures on the order of 0.1 μm at least in one aspect. In one aspect, a method measures a patterned structure. One step of the method is exciting the structure by irradiating it with a spatially periodic laser intensity pattern in order to generate surface acoustic waves. Other steps are diffracting a probe laser beam off a thermal grating to form a signal beam; detecting the signal beam as a function of time to generate a signal waveform; and determining at least one property of the patterned structure based on the effect of the surface profile on surface acoustic wave phase velocity.

In one embodiment, the spatially periodic laser intensity pattern has a period ranging from 1 to 20 microns. In another embodiment, the patterned structure has a surface profile with a period equal to or less than approximately 2 μm.

In one embodiment, the patterned structure is a periodic array of trenches. In another embodiment, the periodic array is a periodic array of linear trenches. In yet another embodiment, the periodic array is a two-dimensional array of trenches.

In one embodiment, the trenches are fabricated in a silicon substrate. In another embodiment, the trenches are fabricated in a thin film.

In one embodiment, the at least one property is trench depth. In another embodiment, the at least one property is trench width. In another embodiment, the at least one property is a depth profile of the trench structure.

In one embodiment, the determining step includes combining measurements at multiple acoustic wavelengths to determine multiple parameters of the trench structure. In another embodiment, the determining step includes measurements along and across the linear trench structure to determine both trench depth and width. In still another embodiment, the determining step includes measurements both within and outside the patterned area in order to separate the effect on the surface acoustic wave velocity caused by the trench structures from the other effects such as film thickness.

In one embodiment, the determining step includes analysis of the signal waveform with a theoretical model based on elastic properties of the structure. In another embodiment, the determining step includes analysis of the signal waveform with an empirical calibration.

The invention provides many advantages that are evident from the following description, drawings, and claims.

The invention may be more completely understood in reference to the following figures:

FIG. 7 depicts a table listing SAW velocity values obtained from the signal waveforms shown in FIG. 6.

According to the current invention, ISTS can be used to measure trench structures with near- or sub-micron width, e.g. a periodic array of trenches etched either in a thin film or in a silicon substrate. The measurement is based on the fact that the SAW phase velocity is affected by the trench structure and is dependent on the parameters of the structure.

According to the invented method, the excitation and detection of SAWs is performed on a patterned sample with surface profile characterized by a period of the order or less than 1 µm. The measurement yields the SAW frequency at a defined wavelength, from which the SAW phase velocity is calculated. The data are analyzed with the help of an analytical or empirical model to determine a parameter of the profile, typically the trench depth or width.

Figure 1:
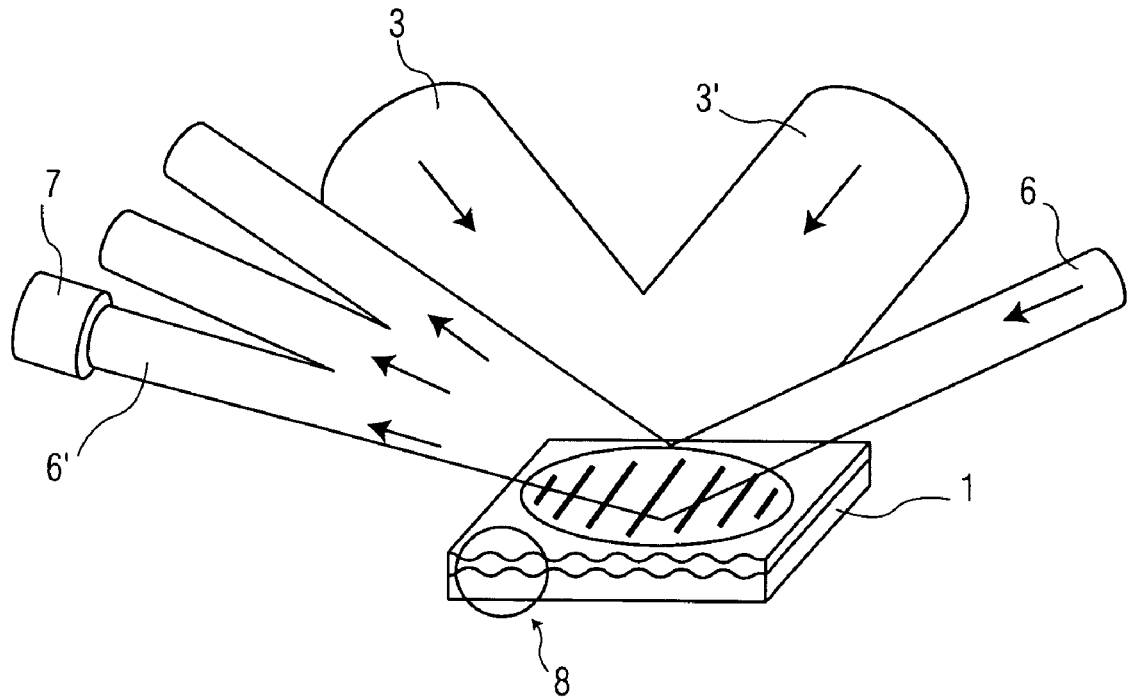
FIG. 1 depicts a thin film structure on an integrated circuit probed using impulsive stimulated thermal scattering according to a prior art method.
Figure 1A:
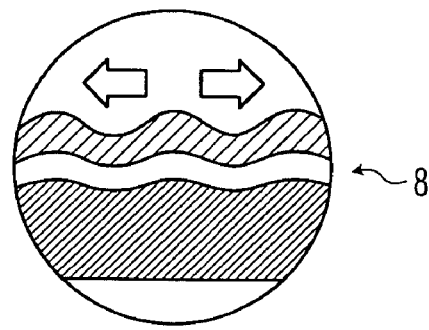
Figure 2A:
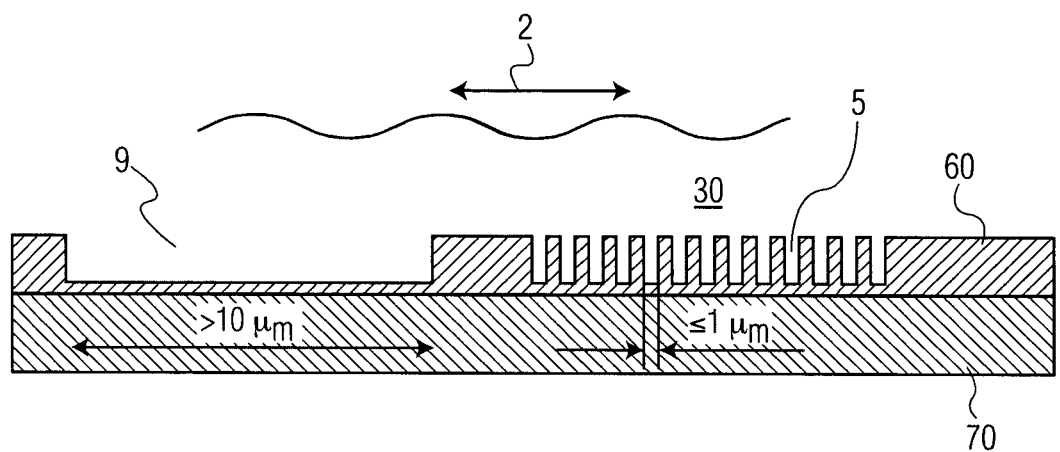
FIG. 2a depicts a patterned film on a silicon substrate.
Figure 2B:
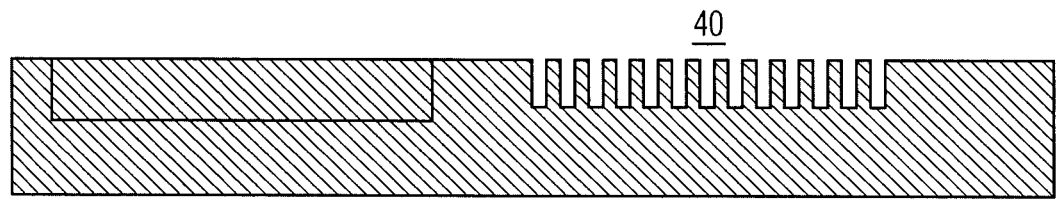
FIG. 2b depicts a patterned silicon substrate.

Accurate analysis of SAW propagation in high aspect ratio trench structures will require finite element calculations. An approximate model can be used in order to obtain an estimate of the effect of high aspect ratio trench array on SAW propagation. The model applies to periodic arrays of linear trenches, such as those labeled 30 and 40 in FIG. 2, with the surface acoustic wave 2 period large compared to the period of the trench structure. Structure (a) of FIG. 2 depicts a periodic array of trenches 30 formed in a thin layer 60 over a substrate 70. Structure (b) of FIG. 2 depicts a periodic array of trenches 40 formed in a silicon substrate. Structure (a) includes a trench 9 on the order of tens of microns. This can be measured by a prior art ISTS method.

The model assumes that if the period of the structure (a) or (b) is small with respect to both SAW 2 wavelength and thickness of the structure, it can be treated as a homogeneous material with effective elastic properties. It is known to calculate the effective elastic properties of a layered structure from the properties of constituent materials, such as in structure (a). The layered structure is effectively described as a transversely isotropic medium with the symmetry axis perpendicular to the layers, which is described by 5 independent effective elastic constants. The same method can be applied to a trench array 30, 40 if vacuum is treated as one of the constituent materials of the structure. Thus, the following equations expressing effective density $\rho^*$ and elastic constants $C_{ij}^*$ of the trench array through the density $\rho$ and elastic constants $C_{ij}$ of the material can be obtained:

$$\rho^* = h\rho \quad (1)$$

$$C_{11}^* = h\left(C_{11} - \frac{C_{12}^2}{C_{11}}\right)$$

$$C_{66}^* = hC_{44}$$

$$C_{13}^* = C_{33}^* = C_{44}^* = 0$$

where h is the ratio of the space between the trenches to the period of the structure. It can be expressed trough the trench width/space ratio as h=1/(1+w/s). The notations in equation (1) assume that the z-axis is perpendicular to the trenches.

Figure 3:
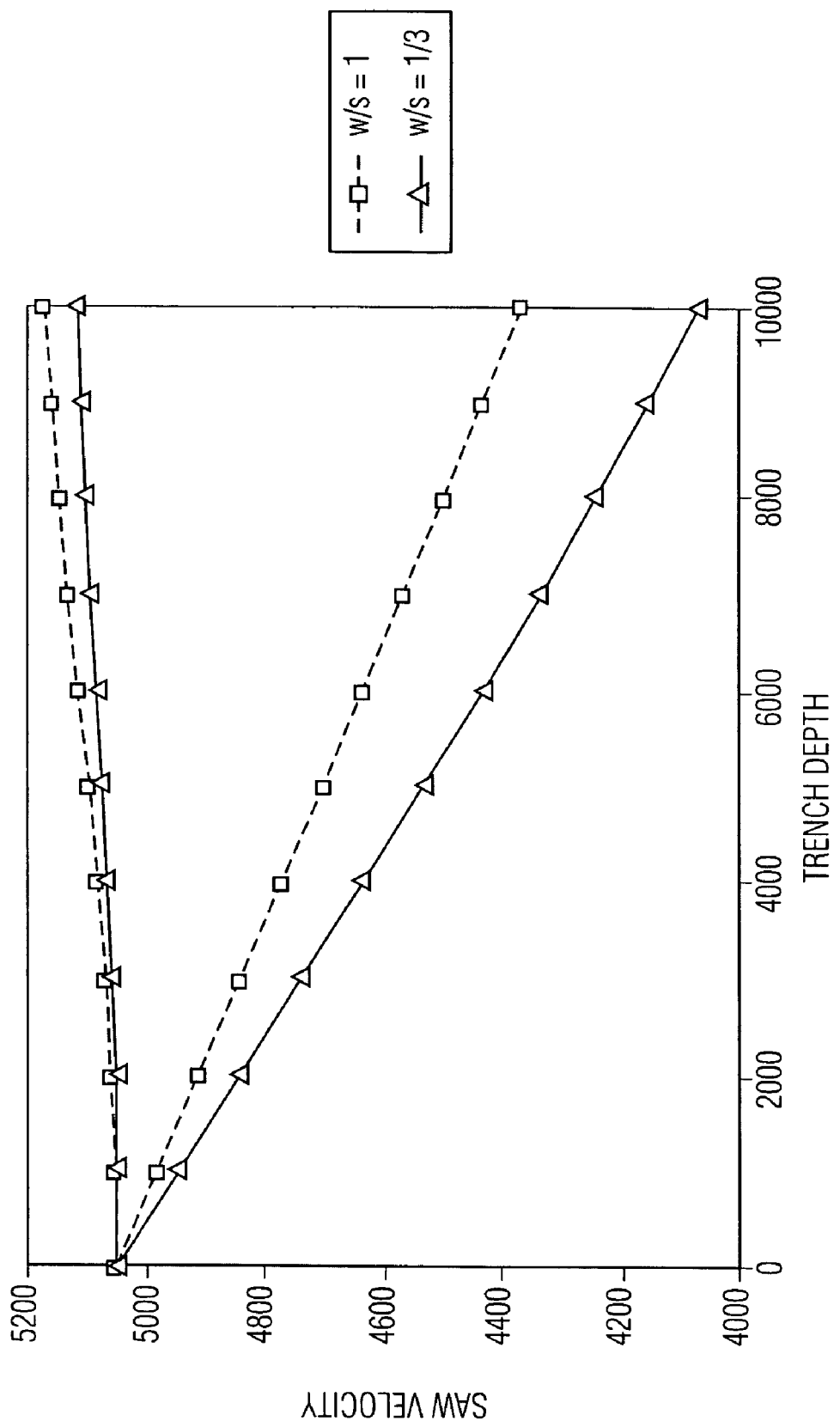
FIG. 3 depicts a matrix indicating calculated dependence of the SAW velocity on trench depth in silicon.
Figure 4:
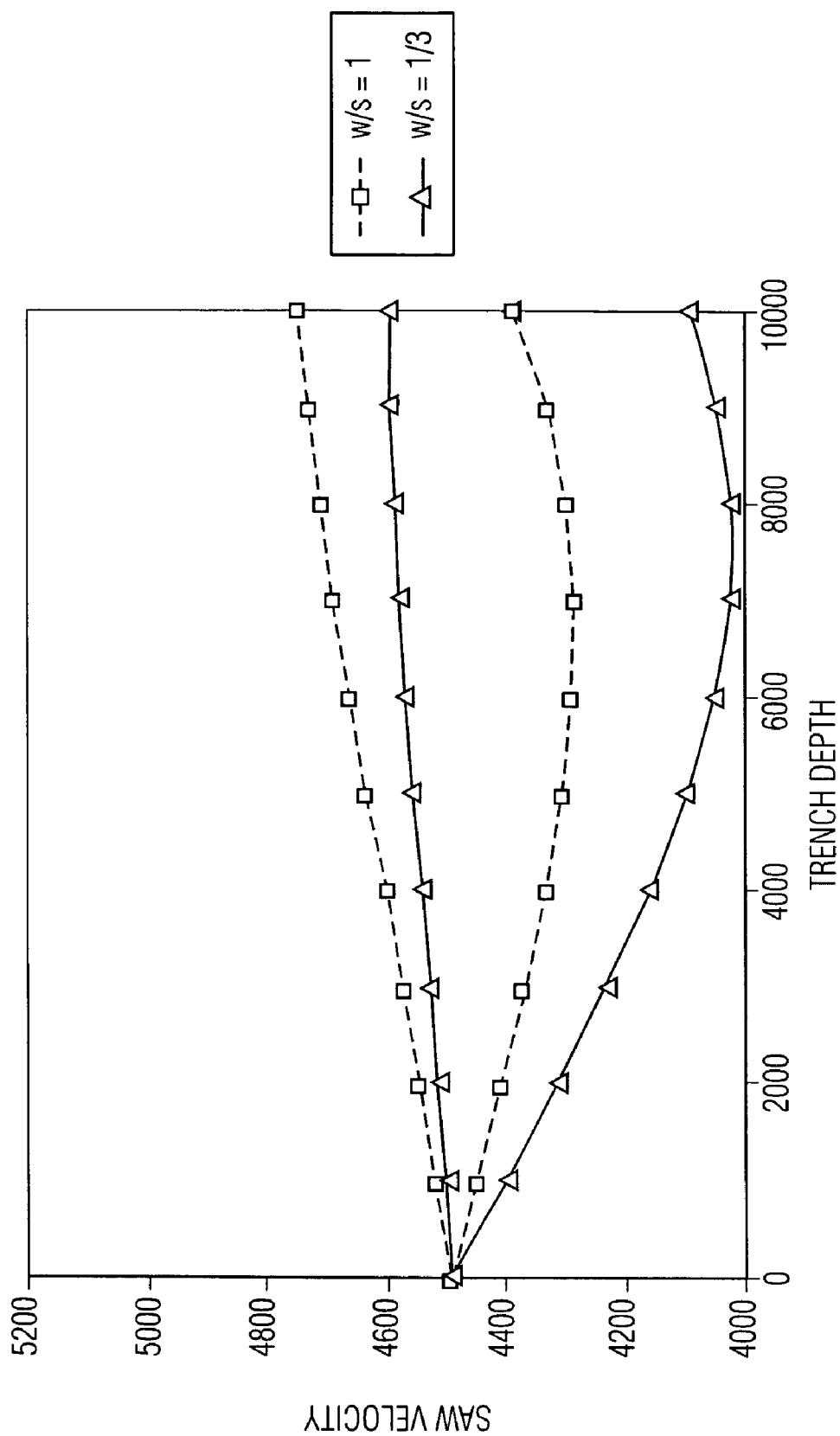
FIG. 4 depicts a matrix indicating calculated dependences of the SAW velocity on trench depth for 1 μm-thick thermal oxide film on a silicon substrate.

FIG. 3 presents the calculated dependence of the SAW velocity on the trench depth for trench arrays with width/space ratios 1:1 and 1:3 fabricated in Si. FIG. 4 depicts the calculated dependence of the SAW velocity on the trench depth for trench arrays in a 1 µm-thick silicon dioxide film on Si. The calculations show that there is a significant dependence of the SAW velocity on both the trench depth 80 and width/space ratio, particularly for SAW propagation across the trenches. In order to estimate the repeatability of the trench depth 80 measurements, assume that the repeatability of the SAW velocity measurements are ~0.5 m/s (which corresponds to the frequency measurement repeatability of 0.1 MHz). For a trench depth of 5000 Å and SAW propagation perpendicular to the trenches, the results presented in FIGS. 3 and 4 yield a repeatability estimate of ~7 Å (or 0.14%) for 1:1 width/space ratio trenches in Si and ~20 Å (or 0.4%) for trenches in the oxide film.

It should be noted that variations in trench depth 80 and width 90 have different effects on SAW velocity parallel ($\parallel$) and perpendicular ($\perp$) to the trenches 5. An increase in the trench width 90 increases the parallel velocity but decreases the perpendicular velocity while an increase in the trench width/space ratio increases the SAW velocity in both directions. This fact indicates that the measurements with SAW propagation along and across the trenches 5 can be combined in order to determine both trench depth 80 and width ratio.

Although the model calculations above applied to a one-dimensional array of linear trenches, it is expected that two-dimensional array of holes will also have an effect of a on the SAW velocity that can be used to measure the parameters of the structure such as trench depth and width.

Performing measurements at multiple SAW wavelengths will provide additional information that can be used for simultaneous measurements of multiple parameters of trench structures. For example, if the SAW wavelength is small compared to the trench depth, SAW velocity will be independent on the trench depth, but still sensitive to the trench width. At longer wavelength, SAW velocity will be sensitive to both trench depth and width. Combining the measurements at short and long wavelengths will thus allow to measure both parameters simultaneously.

Figure 5:
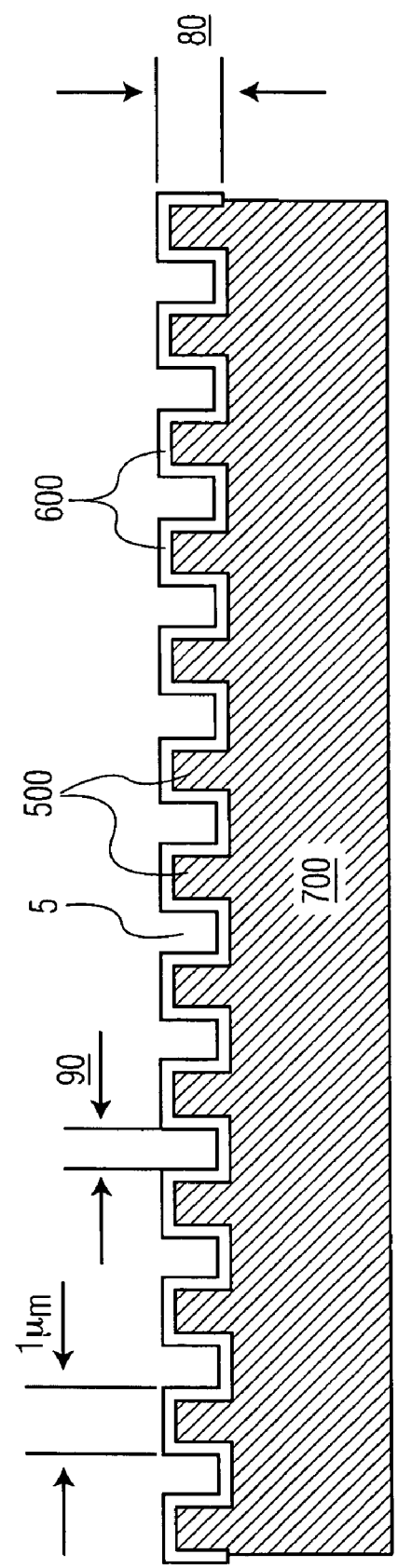
FIG. 5 depicts a structure including a silicon substrate, a trench array etched in a $SiO_2$ film, and a metal film coating.
Figure 6A:
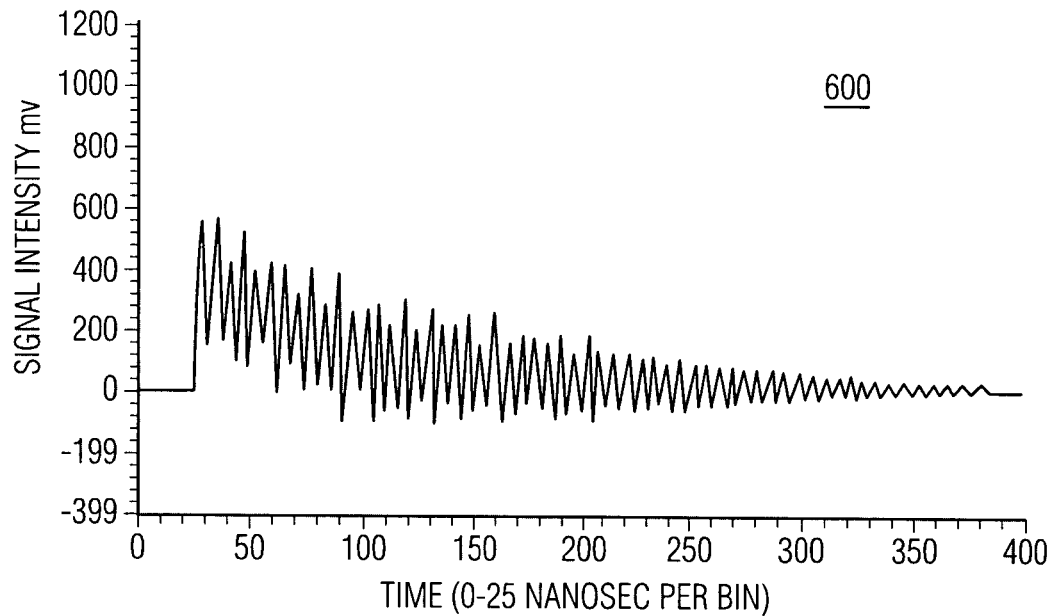
FIG. 6 depicts signal waveforms generated outside of the patterned area of a sample depicted in FIG. 5, parallel to the trenches of a trench array, and perpendicular to the trenches.
Figure 6B:
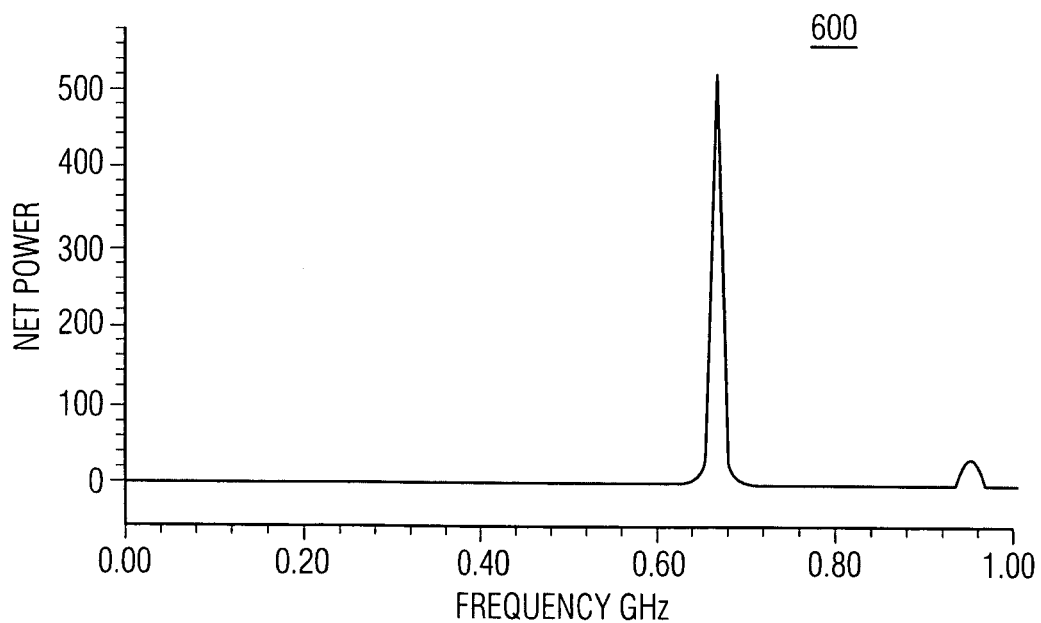
Figure 6C:
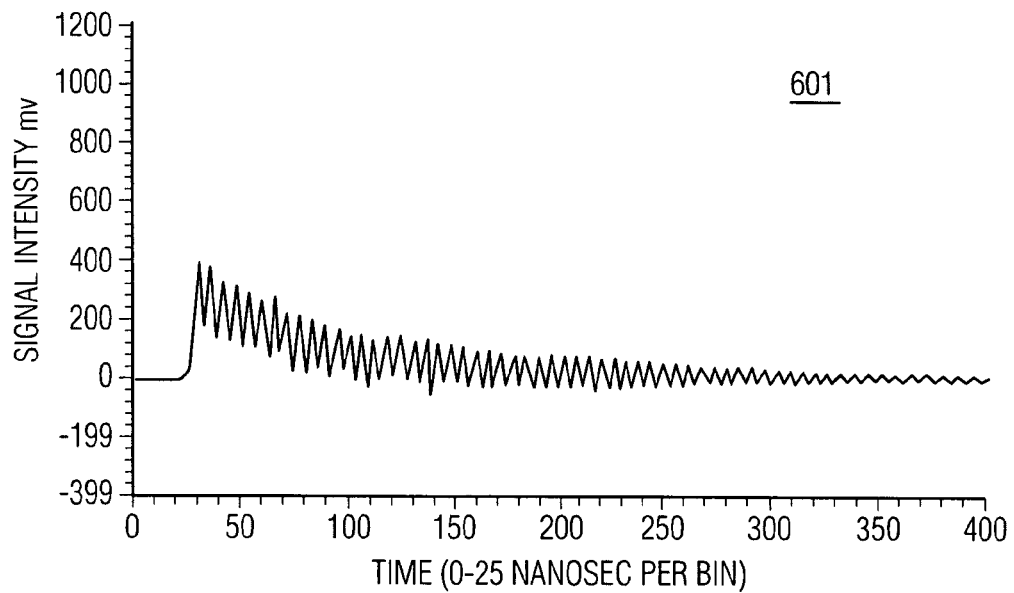
Figure 6D:
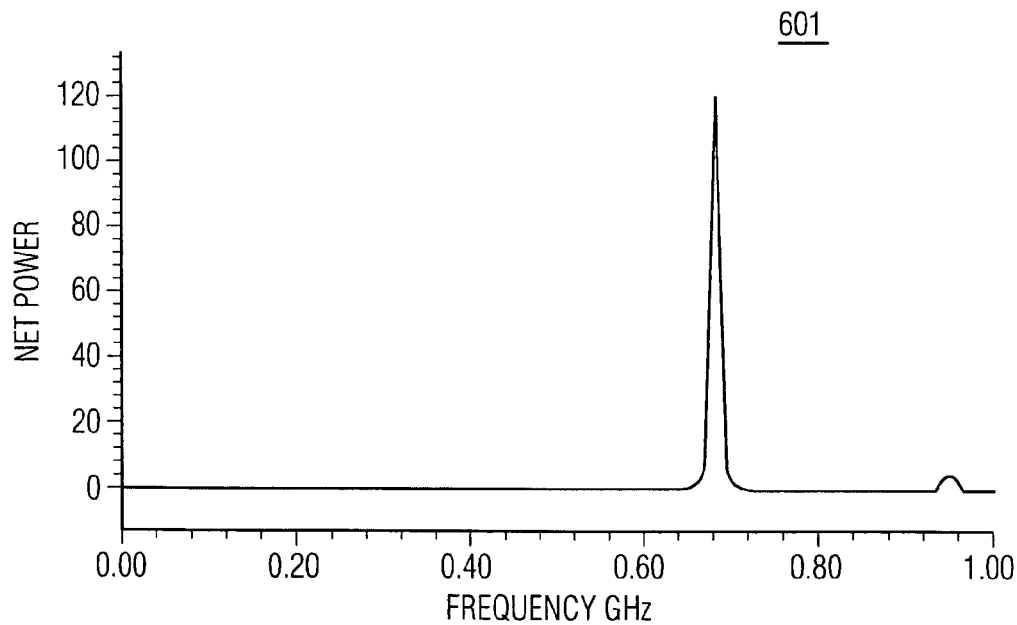
Figure 6E:
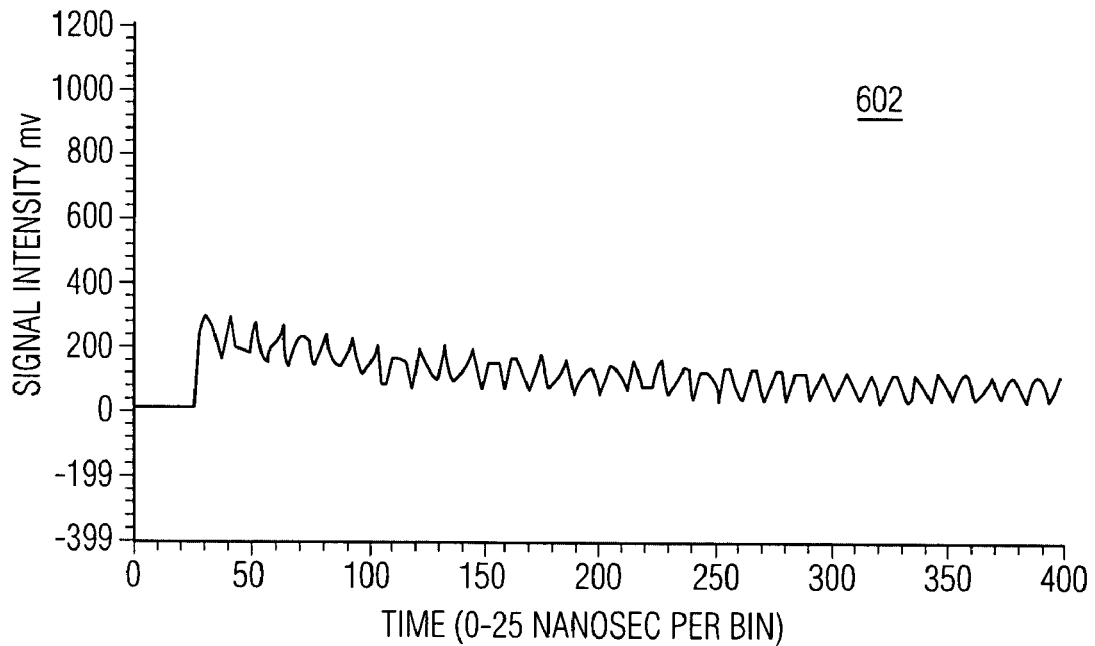
Figure 6F:
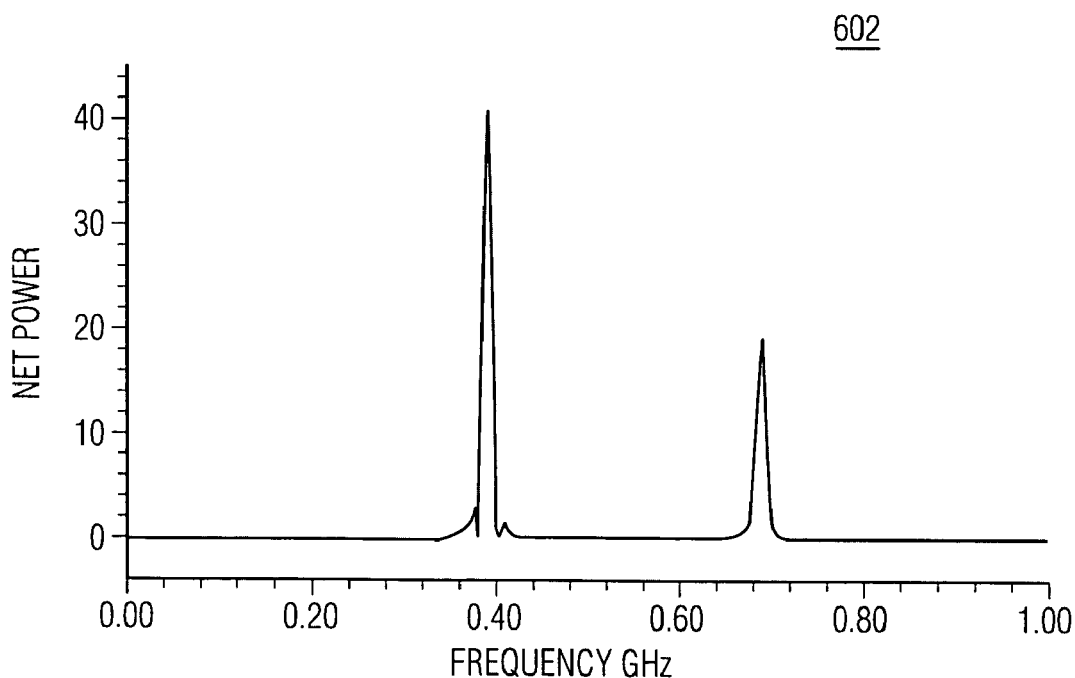

To test the capability of trench measurements with the invented method experimentally, we performed measurements on a structure depicted in FIG. 5 at a SAW wavelength 6 µm. The structure of FIG. 5 includes a substrate 700 formed of silicon, a trench array 500 fabricated in an 800 nm-thick layer of $SiO_2$. The trench width was 1 µm and the width/space ratio was 1:1. The structure was coated with a ~25 nm of Ta and ~100 nm of Cu 600.

FIG. 6 presents the signal waveforms 600 obtained in the unpatterned area of the sample and on the trench array 601, 602 of FIG. 5 with SAW propagation parallel (e.g., 601) and perpendicular (e.g., 602) to the trenches 5. It can be seen from the waveforms 600, 601, 602, that for the perpendicular propagation, the effect of the surface relief on the signal is particularly strong and that it causes a significant decrease in the SAW frequency.

FIG. 7 presents a table listing SAW velocity values obtained from the waveforms shown in FIG. 6. One can see that for the parallel propagation, the SAW velocity increases slightly compared to unpatterned area (i.e. zero trench depth), while for perpendicular propagation the velocity decreases significantly. These results qualitatively agree with the theoretical predictions according to FIG. 4.

The invention provides many additional advantages that are evident from the description, drawings, and claims.

The preceding expressions and examples are exemplary and are not intended to limit the scope of the claims that follow.

The invention claimed is:

1. A method for measuring an unfilled patterned structure (3), the pattern comprising features each having a width dimension, the method comprising:
    irradiating the unfilled patterned structure (3) with a spatially periodic laser intensity pattern in order to excite surface acoustic waves having a wavelength larger than the feature width dimensions;
    diffracting a probe laser beam (6) off the generated surface acoustic waves to form a signal beam;

detecting the signal beam as a function of time to generate a signal waveform;

determining a surface acoustic wave phase velocity from the signal waveform; and determining at least one property of the patterned structure based on the effect of the surface profile of the unfilled patterned structure on the surface acoustic wave phase velocity.

2. The method of claim 1, wherein the unfilled patterned structure comprises a plurality of unfilled trenches.

3. The method of claim 2, wherein the unfilled patterned structure comprises trenches equal to or less than approximately 2 μm in width.

4. The method of claim 3, wherein the unfilled patterned structure further comprises a periodic array of trenches.

5. The method of claim 4, wherein the unfilled patterned structure further comprises a periodic array of linear trenches.

6. The method of claim 4, wherein the unfilled patterned structure further comprises a two-dimensional periodic array of trenches.

7. The method of claim 4, wherein the trenches are fabricated in a silicon substrate.

8. The method of claim 3, wherein the trenches are fabricated in a thin film.

9. The method of claim 2, wherein the at least one property comprises trench depth.

10. The method of claim 2, wherein the at least one property comprises trench width.

11. The method of claim 1, wherein the at least one property comprises a depth profile of the trench structure.

12. The method of claim 1, wherein the determining step further comprises combining measurements at multiple acoustic wavelengths to determine multiple parameters of the unfilled patterned structure.

13. The method of claim 5, wherein the determining step further comprises combining measurements along and across the trench structure to determine both trench depth and width.

14. The method of claim 1, wherein the determining step further comprises combining measurements within and outside the unfilled patterned area to separate the effect on the surface acoustic wave velocity caused by the surface profile from other effects such as film thickness.

15. The method of claim 1, wherein the determining step employs a theoretical model based on effective elastic properties of the structure.

16. The method of claim 1, wherein the determining step employs a model based on an empirical calibration.

17. The method of claim 1, wherein the exciting step further comprises a spatially periodic laser intensity pattern having a period ranging from 1 to 20 microns.

* * * * *